United States Patent
Lee (10) Patent No.: US 10,058,799 B2
(45) Date of Patent: Aug. 28, 2018

(54) PRP EXTRACTION KIT

(71) Applicant: LAON CO., LTD., Siheung-si (KR)

(72) Inventor: Doo Won Lee, Ansan-si (KR)

(73) Assignee: LAON CO., LTD., Siheung-si (KR)

( * ) Notice: Subject to any disclaimer, the term of this patent is extended or adjusted under 35 U.S.C. 154(b) by 0 days.

(21) Appl. No.: 15/313,308

(22) PCT Filed: May 22, 2015

(86) PCT No.: PCT/KR2015/005129
§ 371 (c)(1),
(2) Date: Nov. 22, 2016

(87) PCT Pub. No.: WO2015/178709
PCT Pub. Date: Nov. 26, 2015

(65) Prior Publication Data
US 2017/0189833 A1 Jul. 6, 2017

(30) Foreign Application Priority Data

May 23, 2014 (KR) ........................ 10-2014-0062294

(51) Int. Cl.
*F16K 15/00* (2006.01)
*B01D 21/00* (2006.01)
(Continued)

(52) U.S. Cl.
CPC ..... *B01D 21/0024* (2013.01); *B01D 17/0217* (2013.01); *B01D 17/12* (2013.01);
(Continued)

(58) Field of Classification Search
CPC ............... G01D 17/0217; G01D 17/12; G01D 21/0036; G01D 21/262; G01D 21/0024;
(Continued)

(56) References Cited

U.S. PATENT DOCUMENTS 4,464,254 A * 8/1984 Dojki .................... B01L 3/5021
210/136
5,039,401 A * 8/1991 Columbus ............. B01L 3/5021
137/843

(Continued)

FOREIGN PATENT DOCUMENTS

JP 2007003481 1/2007
KR 1020100105282 9/2010
(Continued)

OTHER PUBLICATIONS

International Search Report—PCT/KR2015/005129 dated Sep. 14, 2015.

*Primary Examiner* — Craig Schneider
*Assistant Examiner* — Kevin Barss
(74) *Attorney, Agent, or Firm* — Novick, Kim & Lee, PLLC; Jae Youn Kim (57) ABSTRACT

Provided is A PRP extraction kit comprises: a body that has an upper accommodation space, a lower accommodation space that is located below the upper accommodation space, and a communication passage which communicates the upper accommodation space and the lower accommodation space and of which a fluid passage area becomes narrower as it goes upward or downward, in the interior thereof; a valve unit that is located in the communication passage and allows flow of the communication passage to go only in one direction while being moved by a self-weight based on a change in a vertical position of the body; and a variation means that is coupled to a lower side of the body and vertically moves based on manipulation of a user to vary the volume of the lower accommodation space.

7 Claims, 5 Drawing Sheets (51) Int. Cl.
    *B01D 17/02*     (2006.01)
    *B01D 17/12*     (2006.01)
    *F16K 15/04*     (2006.01)
    *B01D 21/26*     (2006.01)

(52) U.S. Cl.
    CPC ....... *B01D 21/0036* (2013.01); *B01D 21/262* (2013.01); *F16K 15/04* (2013.01)

(58) Field of Classification Search
    CPC ............ Y10T 137/791; B01D 17/0208; B01D 17/214; B01D 17/0217; B04B 11/00; B04B 11/06; A61M 1/0272; A61M 1/029
    USPC ....... 422/527, 541, 542, 72; 210/512.1, 513, 210/416, 518, 787, 789, 136; 436/177
    See application file for complete search history.

(56) References Cited

U.S. PATENT DOCUMENTS

| | | | |
|---|---|---|---|
| 5,419,835 A * | 5/1995 | Adams | B01L 3/50215 210/515 |
| 6,302,919 B1 * | 10/2001 | Chambers | B01L 3/5021 210/360.1 |
| 6,989,092 B1 * | 1/2006 | Pratt | G01N 1/12 210/136 |
| 8,147,773 B2 * | 4/2012 | Lemme | G01N 1/312 422/501 |
| 8,474,337 B2 * | 7/2013 | Ohtsuka | A61B 10/0038 73/864.71 |
| 9,114,334 B2 * | 8/2015 | Leach | B01D 21/262 |
| 9,533,090 B2 * | 1/2017 | Chavarria | A61M 1/3693 |
| 2005/0186120 A1 * | 8/2005 | Dorian | A61M 1/3693 422/400 |
| 2015/0023939 A1 * | 1/2015 | Woodell-May | B01L 3/502 424/93.71 |

FOREIGN PATENT DOCUMENTS

| | | |
|---|---|---|
| KR | 20110009651 | 1/2011 |
| KR | 101140551 | 5/2012 |
| KR | 101162750 | 7/2012 |
| KR | 200471024 | 1/2014 |

* cited by examiner

PRP EXTRACTION KIT

TECHNICAL FIELD

The present invention relates to a PRP extraction kit and, more particularly, to a PRP extraction kit having a simple structure and economic efficiency.

BACKGROUND ART

In general, a platelet rich plasma (PRP) is obtained by centrifuging blood, removing red blood cells from the blood, and separating a buffy coat layer plentifully containing platelets and growth factors from the blood, and contains platelets and growth factors which are highly concentrated. Because such a PRP functions to reconstruct and regenerate a damaged portion in a blood vessel, the PRP is used as simulants that promote regeneration of skins by highly concentrating the growth factors or promote regeneration of skins as in Prolotherapy to reconstruct and regenerate skins or tissues (ligaments and tendons), so that the PRP is effective in treating joint inflammation, chronic back pain, pelvic pain, damages to ligaments of shoulders or keens, and the like.

Meanwhile, as the related art for extracting the PRP, a buffy coat extraction kit including a kit body that has a plasma part, a buffy coat part, and a red blood cell part, a stopper that is coupled to an upper end of the kit body, and a piston that is coupled to the kit body to forward or rearward move along an axial direction of the kit body, in the interior thereof, is disclosed in Korean Patent Registration No. 1140551. However, because the buffy coat extraction kit according to the related art inserts a needle of an extraction syringe into an inner deep location where buffy coats are situated using the extraction syringe after centrifugation, and extracts the buffy coats, there is a problem in that the operation is complex and difficult.

Further, unlike this, a blood separation and concentration container for PRP and filter extraction and fibrin generation, which includes a main body, an upper cover, a lower cover, and a needle penetration part, is disclosed in Korean Laid-Open Patent No. 10-2010-0105282. In this case, there are disadvantages in that because a structure thereof is complex, economic efficiency and productivity thereof deteriorate and a using method therefor is difficult and complex.

That is, the buffy coat extraction kit according to the related art has a problem in that it is difficult for an unskilled worker to use the kit because an operation of extracting buffy coat, including, for example, an operation of manipulating the needle penetration part, is difficult and a using method therefor is complex, and has a problem in that because a structure thereof is complex, a using method therefor is difficult and complex, and manufacturing costs are raised so that economic efficiency thereof thus deteriorates as well.

DISCLOSURE

Technical Problem

An aspect of the present invention is to provide a PRP extraction kit that easily extracts buffy coats, has a simple structure so that a use thereof is convenient, and may also improve productivity.

Technical Solution

The present invention provides a PRP extraction kit including a body that has an upper accommodation space, a lower accommodation space that is located below the upper accommodation space, and a communication passage which communicates the upper accommodation space and the lower accommodation space and of which a fluid passage area becomes narrower as it goes upward or downward, in the interior thereof, a valve unit that is located in the communication passage and allows flow of the communication passage to go only in one direction while being moved by a self-weight based on a change in a vertical position of the body, and a variation means that is coupled to a lower side of the body and vertically moves based on manipulation of a user to vary the volume of the lower accommodation space.

Here, the PRP extraction kit further includes an upper cap that is coupled to an upper side of the body to close the upper accommodation space, and a lower cap that is coupled to a lower side of the body to close the lower accommodation space, and has the variation means.

At this time, the upper cap is detachably coupled to the upper side of the body and has an extraction hole that extends from the outside to communicate the upper accommodation space and the outside.

Meanwhile, the lower cap has a cup shape of which an upper portion is opened and of which an upper inner peripheral surface is coupled to a lower outer peripheral surface of the body, and the variation means corresponds to screws that are formed on the lower outer peripheral surface of the body and an upper inner peripheral surface of the lower cap, which faces the lower outer peripheral surface of the body, respectively, and varies the volume of the lower accommodation space as the lower cap vertically moves when the user rotates the lower cap.

Further, the lower cap has a pressing part that protrudes upward from an upper bottom surface of the lower cap.

Furthermore, it is preferred that the communication passage has a circular fluid passage area, and a spherical ball valve is applied to the valve unit.

Further, the body includes a first body that has an accommodation space formed therein and has a separator plate that is integrally formed therein to divide the accommodation space into the lower accommodation space and an upper space and has one or a plurality of communication holes that communicate the lower accommodation space and the upper space, and a communication member that is inserted into the upper space of the first body, has the upper accommodation space formed therein, communicates with the communication holes in a central portion of a bottom surface thereof, and has the communication passage.

Further, the PRP extraction kit includes an airtight member that is provided at a portion where the first body and the second body are in surface contact with each other, to maintain airtightness between the first body and the second body.

Advantageous Effects

A PRP extraction kit according to the present invention provides the following effects.

First, the PRP extraction kit may easily extract buffy coats, thereby improving workability, and may enable an unskilled person to easily perform the extraction.

Second, the PRP extraction kit has a simple structure including a ball valve, so that production costs may be reduced, and productivity and economic efficiency may be thus improved.

Third, the PRP extraction kit has a simple structure and may easily extract a PRP only through a simple process, so that use thereof is convenient.

DESCRIPTION OF THE INVENTION

<Description of Main Elements of Drawings>

| | |
|---|---|
| 100: Body | 101: Upper accommodation space |
| 102: Lower accommodation space | 103: Communication passage |
| 110: First body | 111: Upper space |
| 112: Separator plate | 114: Communication hole |
| 116: Seating part | 120: Second body |
| 122: Communication member | 124: Communicating port |
| 130: Airtight member | 200: Valve unit |
| 210: Ball valve | 300: Variation means |
| 310: Screw | 400: Upper cap |
| 401: Thread | 402: Sealing member |
| 410: Extraction hole | 500a, 500b: Lower caps |
| 511: First pressing member | 512: Second pressing member |
| 510a, 510b: Pressing parts | 600, 700: PRP extraction kits |

BEST MODE

Hereinafter, exemplary embodiments of the present invention will be described in detail with reference to the accompanying drawings.

Figure 1:
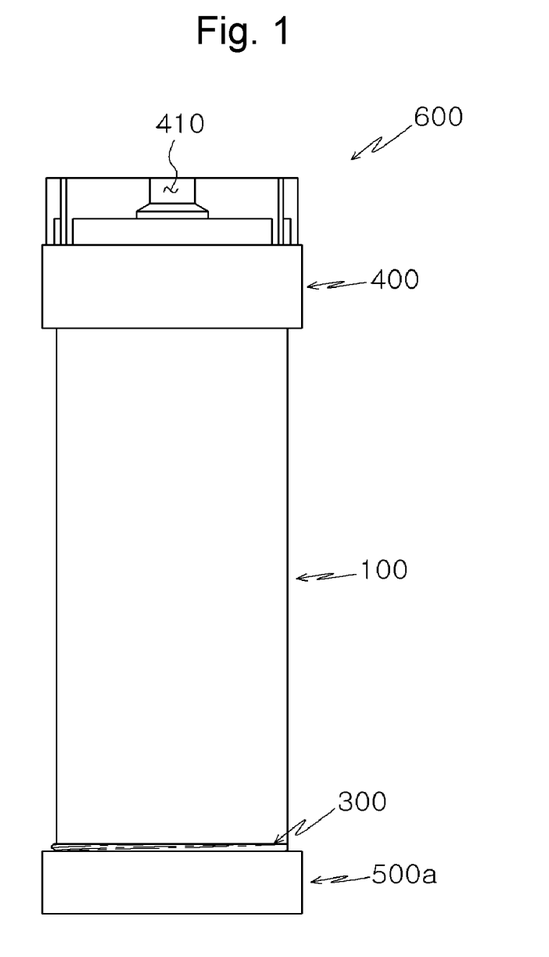
FIG. 1 is a front view illustrating an outer appearance of a PRP extraction kit according to an embodiment of the present invention.
Figure 2:
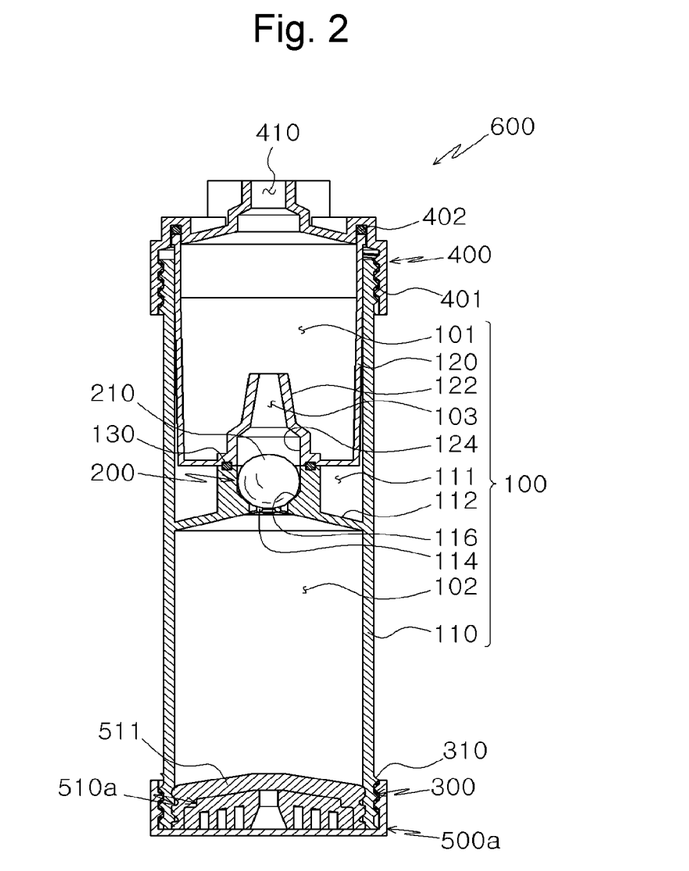
FIG. 2 is a sectional view illustrating an internal structure of the PRP extraction kit of FIG. 1.

Referring to FIGS. 1 and 2, a PRP extraction kit 600 according to a first embodiment of the present invention includes a body 100, a valve unit 200, a variation means 300, an upper cap 400 and a lower cap 500a.

First, the body 100 has an approximately cylindrical shape, and includes an upper accommodation space 101 that is formed on an inner upper side thereof, a lower accommodation space 102 that is formed on an inner lower side thereof and is located below the upper accommodation space 101, and a communication passage 103 which is located on an inner central side thereof and communicates the upper accommodation space 101 and the lower accommodation space 102.

Here, the communication passage 103 has a flow area narrower than those of the upper accommodation space 101 and the lower accommodation space 102 and a fluid passage area becomes narrower as it goes upward or downward such that the valve unit 200 may be located therein.

Meanwhile, the body 100 includes a first body 110 and a second body 120 that is inserted into and assembled with the first body 110, which are separated from each other with reference to the communication passage 103 such that the valve unit 200 is located in the communication passage 103.

In more detail, the first body 110 has an approximately cylindrical shape and has an accommodation space formed therein and a separator plate 112 that protrudes inward from an inner central location thereof and divides the accommodation space into the lower accommodation space 102 and an upper space 111.

Here, it is preferred that the separator plate 112 is inclinedly formed to have a funnel shape that becomes narrower as it goes upward in consideration of fluid resistance and the like when fluid flows in a direction of the communication passage 103.

Further, the separator plate 112 is integrally formed with the first body 110 and has one or a plurality of communication holes 114 that communicates the lower accommodation space 102 and the upper space 110 and a seating part 116 which protrudes upward and has a shape corresponding to a shape of a flat cross-section of the valve unit 200 and on which the valve unit 200 is seated.

The second body 120 has an approximately cup shape, has the upper accommodation space 101 formed therein, and is inserted into the upper space 111 of the first body 110 such that an outer bottom surface and an outer peripheral surface thereof are assembled to be close contact with an inner surface of the first body 110.

Meanwhile, the second body 120 has a communicating port 124 that communicates with the communication hole 114 on a central portion of a bottom surface thereof and corresponds to the shape of the flat cross-section of the valve unit 200 and a communication member 122 that integrally protrudes towards a side of a window along the communicating port 124.

The communication member 122 has an approximately tube shape, is connected to a space of the seating part 116 in the interior thereof, is formed to have a shape of which a fluid passage area becomes narrower as it goes upward, thus forms the communication passage 103, and prevents the valve unit 200 from being separated therefrom when the body 100 is vertically reversed as well.

Meanwhile, the PRP extraction kit 600 has an airtight member 130 that maintains airtightness between the first body 110 and the second body 120. Here, the airtight member 130 is formed at a portion where the bottom surface of the second body 120 and an upper surface of the seating part 116 face each other. It is preferred that an O-ring is applied to the airtight member 130 but the present invention is not limited thereto.

Further, it is preferred that the first body 110 and the second body 120 are formed of a transparent material such that inner fluid may be easily identified from the outside.

The valve unit 200 is located in the communication passage 103 and serves to allow the flow of the communication passage 103 to go only in one direction while being moved by a self-weight based on a change in a vertical position of the body. Here, any materials that have a higher density than that of the fluid and may be lowered by the self-weight within the fluid may be applied to the valve unit 200.

Meanwhile, it is preferred that the communication passage 103 has a circular fluid passage area and a spherical ball valve 210 may be applied to the valve means corresponding to the communication passage 103. The ball valve may be easily processed, may further reduce a fluid resistance when moving in the fluid, and may more effectively close the communication passage 103 in one direction when being seated.

The variation means 300 is located below the body 100 and serves to vary a volume of the lower accommodation space 102 as the variation means 300 vertically moves by manipulation of a user. Here, the variation means 300 may be located below the body 100 and may be configured as a separate configuration such as a piston. However, as will be described below, the variation means 300 may be integrally provided with the lower cap 500*a* and thus is simple and convenient, making it possible to vary the volume of the lower accommodation space 102. Detailed descriptions thereof will be made below.

It is preferred that the upper cap 400 has a thread 401 that is formed on an upper outer peripheral surface of the upper cap 400 such that the upper cap 400 may be attached/detached to/from the body 100 and that is engaged with an inner peripheral surface of the upper cap 400, which faces the upper outer peripheral surface, so that the upper cap 400 may be easily attached/detached to/from the body 100 by manipulation of the user. However, it is apparent that in addition to the above-described thread 401, various configurations which may achieve the above-described object, including, for example, a structure that is slide-fitted in a snap scheme, may be applied as a means for further improving a fastening force.

Meanwhile, the upper cap 400 has an extraction hole 410 that extends from the outside to communicate the upper accommodation space and the outside. The extraction hole 410 enables the inner fluid to be easily extracted using an extractor from the outside without separating the upper cap 400. Here, although not illustrated, a stopper that opens/closes the extraction hole 410 may be provided, the well-known rubber stopper or the like may be used as a configuration of the stopper, and detailed descriptions thereof will be omitted.

The upper cap 400 has a sealing member 402 that is formed at a portion facing the upper surface of the second body 120 to maintain airtightness of the upper accommodation space 101, and the well-known O-ring or the like may be applied to the sealing member 402.

The lower cap 500*a* has an approximately cup shape, an upper portion of which is opened, and is coupled to a lower side of the body to serve to close the lower accommodation space 102. In detail, a lower outer peripheral surface of the body 100 is detachably coupled to an upper inner peripheral surface of the lower cap 500*a*.

Meanwhile, because the lower cap 500*a* has the variation means 300, and the variation means 300 may simultaneously serve as a means by which the lower cap 500*a* and the body 100 may be attached/detached to/from each other, detailed descriptions thereof will be made in detail when the variation means 300 is described.

The variation means 300 is formed by screws 310 that are formed on a lower outer peripheral surface of the body 100 and an inner peripheral surface of the lower cap 500*a*, which faces the lower outer peripheral surface of the body 100, and are engaged with each other. Accordingly, when the user rotates the lower cap 500*a*, the lower cap 500*a* varies the volume of the lower accommodation space 102 while being vertically moved by the variation means 300.

That is, when the user rotates the lower cap 500*a* in one direction, the lower cap 500*a* moves upward and a bottom surface thereof is thus raised so that the volume of the lower accommodation space 102 is reduced. In contrast, when the user rotates the lower cap 500*a* in a downward direction, the lower cap 500*a* moves downward and the bottom surface thereof is thus lowered so that the volume of the lower accommodation space 102 is increased. In this way, as the user varies the volume of the lower accommodation space 102 through the variation means 300, fluid accommodated in the lower accommodation space 102 flows to the communication passage 103 while upward moving along the communication hole 114.

Meanwhile, considering that the volume of the lower accommodation space 102 is varied as the upper bottom surface of the lower cap 500*a* is raised/lowered by the variation means 300, it is preferred that the lower cap 500*a* has a pressing part 510*a* that protrudes upward from the upper bottom surface and presses the fluid in the lower accommodation space 102 to upward move the fluid.

The pressing part 510*a* includes a first pressing member 511, a bottom surface of which is seated on the upper bottom surface of the lower cap 500*a* and an outer peripheral surface of which is coupled to be close contact with an inner peripheral surface of an opened lower inner peripheral surface of the first body 110, and vertically moves in conjunction with the lower cap 500*a* when the lower cap 500*a* vertically moves by the variation means 300, to vary the volume of the lower accommodation space 102.

Figure 3:
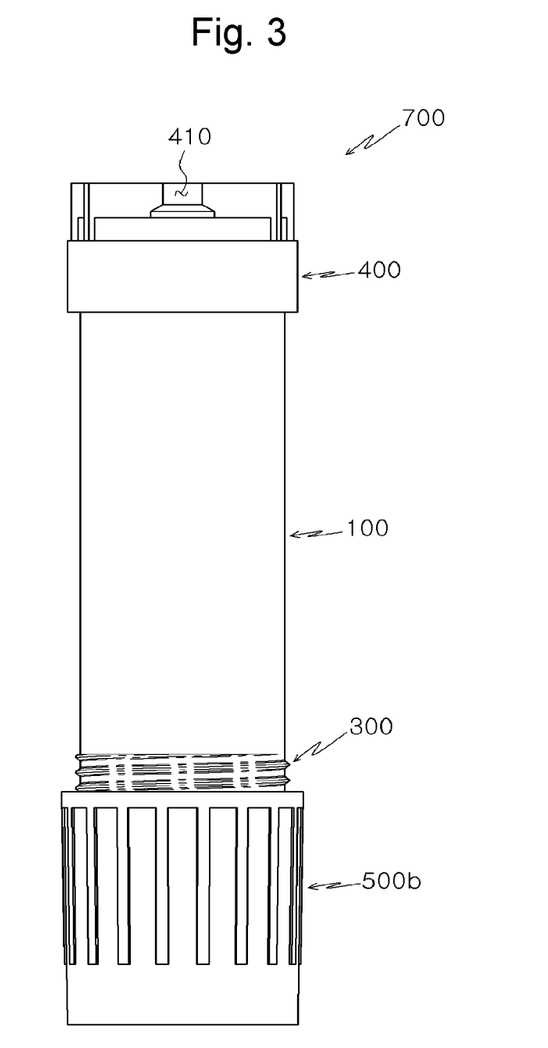
FIG. 3 is a front view illustrating an outer appearance of a PRP extraction kit according to another embodiment of the present invention.
Figure 4:
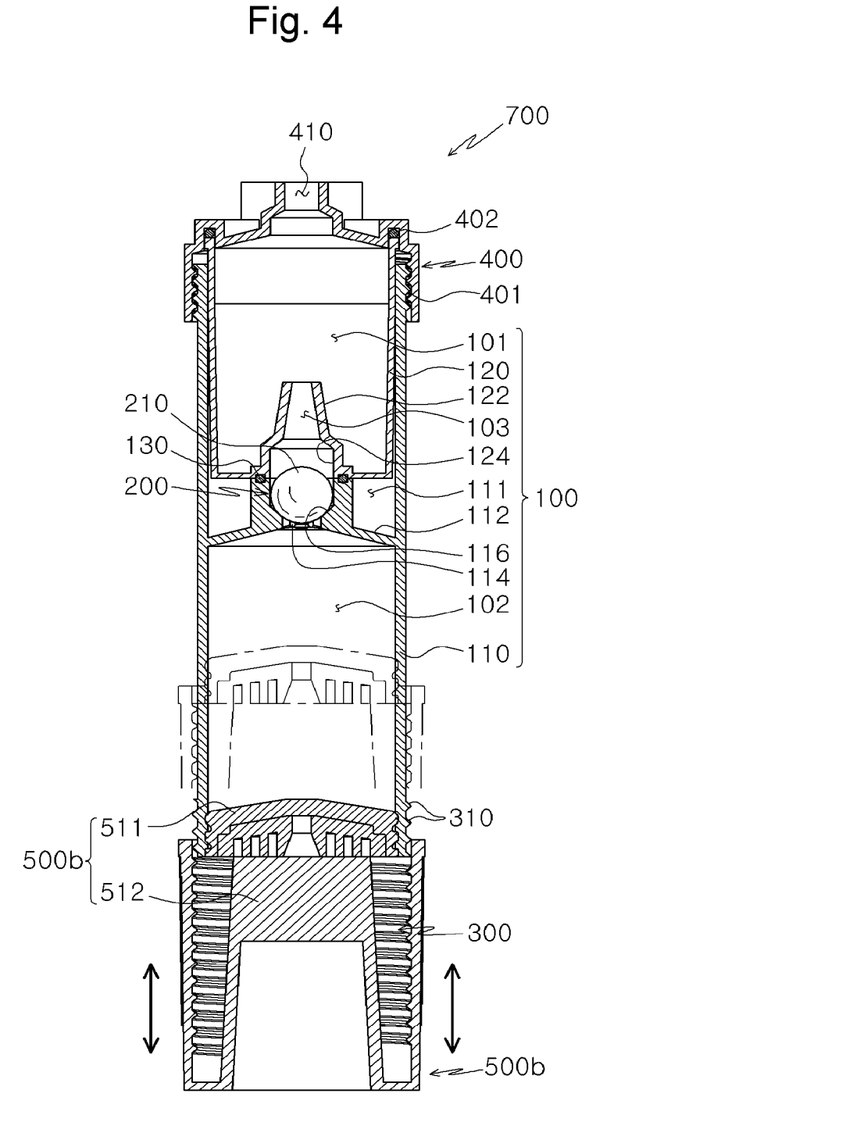
FIG. 4 is a sectional view illustrating an internal structure of the PRP extraction kit of FIG. 3.

Referring to FIGS. 3 and 4, the pressing part 510*b* may further include a second pressing member 512 that protrudes upward to improve compressibility of the fluid, in addition to the first pressing part 511.

The second pressing member 512 protrudes upward from the bottom surface of the lower cap 500*b* and the first pressing member 511 is seated on an upper surface thereof. Here, as illustrated, the second pressing member 512 may have a shape that becomes narrower as it goes upward and may also have an empty space formed on the bottom surface thereof to reduce material costs. However, said feature is merely an exemplary embodiment, and it is apparent that various configurations that may achieve the above objects may be applied thereto.

Meanwhile, a PRP extraction kit 700 according to a second embodiment is another embodiment that is made due to the pressing part 510*b*. Because configurations of the PRP extraction kit 700 according to the second embodiment, except for the pressing part 510*b*, are similar to those of the PRP extraction kit 600 according to the first embodiment, detailed descriptions thereof will be omitted, and the same reference numerals designate the same members.

Hereinafter, a method for extracting a buffy coat using the PRP extraction kit 700 according to the second embodiment will be described.

Figure 5:
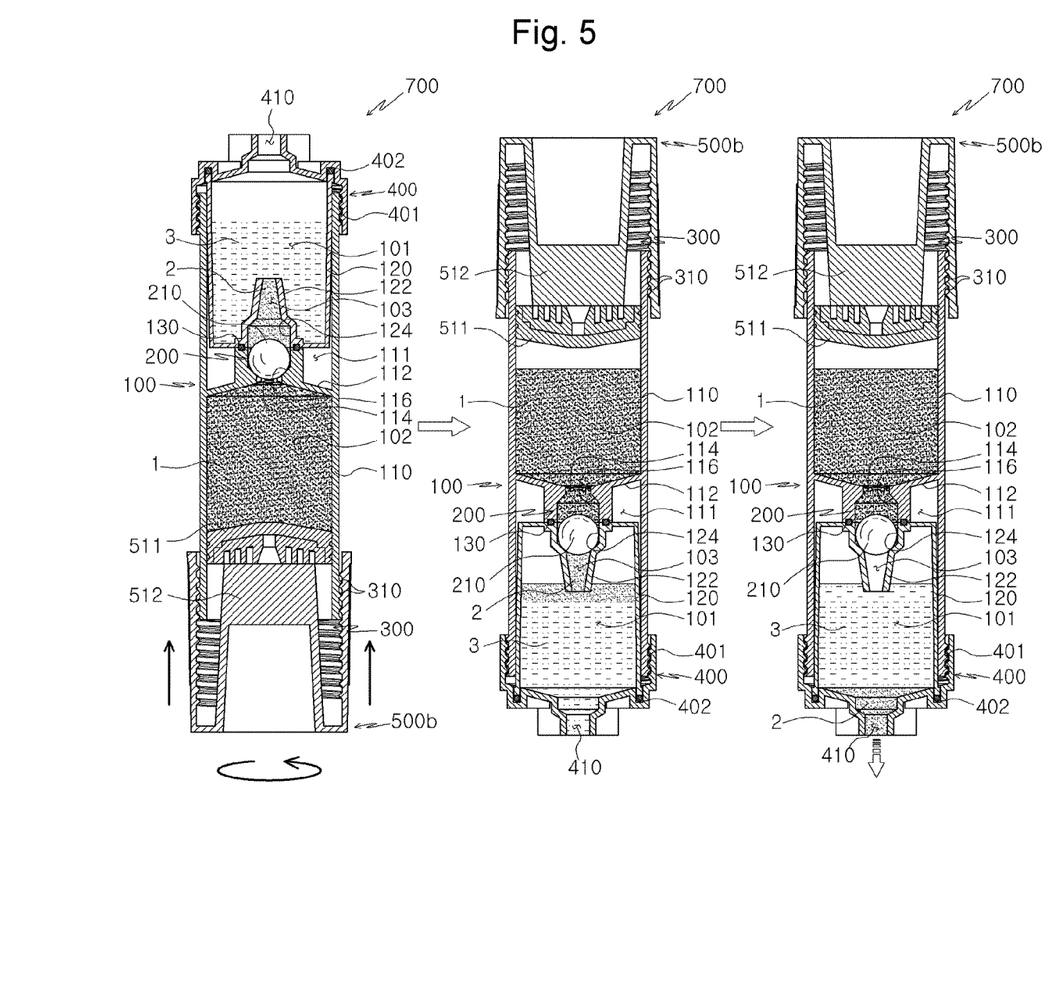
FIG. 5 is a sectional view illustrating a PRP extracting process using the PRP extraction kit of FIG. 3.

Referring to FIG. 5, after blood is injected into the body 100, the blood is centrifuged, and the centrifuged blood is separated from each other in an order of blood cells 1, buffy coats 2, and blood plasmas 3 from below.

Further, when the lower cap 500*b* is rotated through the variation means 300, the blood flows upward by the pressing part 510*b* as the lower cap 500*b* moves upward. Here, when the blood flows through the variation means 300, the blood flows such that the blood cells 1 are located on a lower side of the valve unit 200 and the buffy coats 2 and the blood plasmas 3 are located on an upper side of the valve unit 200. (see FIG. 5A)

Next, as the body 100 is vertically reversed, the upper accommodation space 101 is located on a lower side and the lower accommodation space 102 is located on an upper side. Here, as the valve unit 200 is lowered by a self-weight, the blood cells 1 are continuously located on the upper side while staying in the lower accommodation space 102, and the buffy coats 2 and the blood plasmas 3 in the upper accommodation space 101 are located on the lower side in an order of the blood plasmas 3 and the buffy coats 2 from below.

Here, because the valve unit 200 allows only upward flow and disallows downward flow, fluid on an upper side does not flow to a lower side when the body 100 is reversed. (See FIG. 5B)

Thereafter, in this state, centrifugation is performed again, and the buffy coats 2 and the blood plasmas 3 are thus located in the upper accommodation space 101 in an order of the buffy coats 2 and the blood plasmas 3 from below. Then, the buffy coats 2 are located on the lowest side, and thus, only the buffy coats 2 may be easily extracted through the extraction hole 410. (See FIG. 5C)

As described above, because the PRP extraction kits 600 and 700 need not to perform extraction by deeply inserting a separate syringe into the body 100 and may separate the buffy coats 2 only through a simple process without a particular operation through one time of a vertical reversal of the body 100 and centrifugation, the buffy coats 2 may be easily extracted, so that an unskilled person may also easily perform the extraction as well as a workability may be improved. Further, as described above, because the PRP extraction kits 600 and 700 have a simple structure including the valve unit 200, manufacturing costs may be reduced so that productivity and economic efficiency thereof may be improved.

Although the present invention has been described with reference to embodiments illustrated in the accompanying drawings, the embodiments are merely exemplary. Further, it will be understood by those skilled in the art to which the present invention pertains that the present invention may be variously corrected and modified without departing from the spirit and area of the present invention claimed in the claims.

The invention claimed is:

1. A PRP extraction kit comprising:
    a body that has an upper accommodation space, a lower accommodation space that is located below the upper accommodation space, and a communication passage which communicates the upper accommodation space and the lower accommodation space and includes a fluid passage area becoming narrower as it goes upward or downward, in an interior thereof;
    a valve unit that is located in the communication passage and allows a flow in the communication passage to go only in one direction while being moved by a self-weight based on a change in a vertical position of the body;
    a variation means that is coupled to a lower side of the body and vertically moves based on manipulation of a user to vary a volume of the lower accommodation space;
    an upper cap that is coupled to an upper side of the body to close the upper accommodation space; and
    a lower cap that is coupled to a lower side of the body to close the lower accommodation space, and has the variation means.

2. The PRP extraction kit according to claim 1, wherein the upper cap is detachably coupled to the upper side of the body and has an extraction hole that extends from an outside to communicate the upper accommodation space and the outside.

3. The PRP extraction kit according to claim 1, wherein the lower cap has a cup shape of which an upper portion is opened and of which an upper peripheral surface is coupled to a lower outer peripheral surface of the body, and
    wherein the variation means corresponds to screws that are formed on the lower peripheral surface of the body and an inner peripheral surface of the lower cap, which faces the lower peripheral surface of the body, respectively, and varies the volume of the lower accommodation space as the lower cap vertically moves when the user rotates the lower cap.

4. The PRP extraction kit according to claim 1, wherein the lower cap has a pressing part that protrudes upward from an upper bottom surface of the lower cap.

5. The PRP extraction kit according to claim 1, wherein the fluid passage area has a circular fluid passage area, and the valve unit is a spherical ball valve.

6. The PRP extraction kit according to claim 5, wherein the body comprises:
    a first body that has the lower accommodation space and an upper space formed therein and has a separator plate that is integrally formed therein to divide the lower accommodation space from the upper space and has one or a plurality of communication holes that communicate the lower accommodation space and the upper accommodation space, and
    a second body that is inserted into the upper space of the first body, has the upper accommodation space formed therein, and has a communication member that is formed in a central portion of a bottom surface of the second body to communicate with the communication holes and has the communication passage.

7. The PRP extraction kit according to claim 6, further comprising:
    an airtight member that is provided at a portion where the first body and the second body are in surface contact with each other, to maintain airtightness between the first body and the second body.

* * * * *